United States Patent
Rambach

(10) Patent No.: US 6,548,268 B1
(45) Date of Patent: Apr. 15, 2003

(54) **CHROMOGENIC MEDIUM FOR DETECTING *STAPHYLOCOCCUS AUREUS***

(76) Inventor: Alain Rambach, 73, Bd Montparnasse, 75006 Paris (FR)

(*) Notice: Subject to any disclaimer, the term of this patent is extended or adjusted under 35 U.S.C. 154(b) by 0 days.

(21) Appl. No.: 09/936,486

(22) PCT Filed: Mar. 9, 2000

(86) PCT No.: PCT/FR00/00583

§ 371 (c)(1), (2), (4) Date: Jan. 28, 2002

(87) PCT Pub. No.: WO00/53799

PCT Pub. Date: Sep. 14, 2000

(30) Foreign Application Priority Data

Mar. 11, 1999 (FR) .............................. 99 03003

(51) Int. Cl.[7] .............................. C12Q 1/04; C12Q 1/00; C12N 1/00
(52) U.S. Cl. .............................. 435/34; 435/14; 435/883
(58) Field of Search .............................. 435/34, 14, 883

(56) References Cited

FOREIGN PATENT DOCUMENTS

| FR | 2747394 A | | 10/1997 |
|----|-----------|---|---------|
| WO | WO 9212259 A | | 7/1992 |
| WO | WO 9504157 A | | 2/1995 |
| WO | WO 9520674 A | | 8/1995 |
| WO | WO 9832874 A | | 7/1998 |
| WO | WO 00/53799 | * | 9/2000 |

OTHER PUBLICATIONS

Lindsay J. A; Aravena–Roman M A; Riley TV: "Identification of Staphylococcus epidermidis and Staphyloccus hominis from blood cultures by testing susceptibility to desferrioxamine" European Journal of Clinical Microbiology & Infectious Diseases, vol. 12, 1993, pp. 127–131.

Heuck Dagmar; Witte Wolfgang; Braulke Christine; Reissbrodt Rolf: "Susceptibility to desferrioxamines and other chelators of coagulase–negative staphylocci" Zentralblatt Fuer Bakteriologie, vol. 280, 1994, pp. 304–311, XP000921273 tableux 2,3.

Mulder J G: "A simple and inexpensive method for the identification of Staphylococcus epidermidis and Staphyloccus hominis"European Journal of Clinical Microbiology & Infectious Diseases, vol. 14, 1995, pp. 1052–1056, XP000921270.

DL Stevens, C Jones: "Use of trehalose–mannitol–phosphatase agar to differentiate Staphyloccus aureus and Staphyloccus saprophyticus", Journal of Clinical Microbiology, vol. 20, 1984, pp. 977–980, XP000856420.

* cited by examiner

*Primary Examiner*—Louise N. Leary
(74) *Attorney, Agent, or Firm*—Blakely, Sokoloff, Taylor & Zafman

(57) ABSTRACT

The invention concerns a novel chromogenic medium for isolating *Staphylococcus aureus,* charcterised in that it comprises in a culture medium of *Staphyloccus aureus* at least one of the following two chromogenic agents: 5-bromo 6-chloro 3-indoxyl phosphate and 5-brono 4-chloro 3-indoxyl glucoside and it further contains deferoxamine.

4 Claims, No Drawings

CHROMOGENIC MEDIUM FOR DETECTING STAPHYLOCOCCUS AUREUS

The present invention relates to a novel chromogenic medium intended to reveal Staphylococcus aureus.

Staphylococcus aureus is a bacterium, the detection of which is proving to be increasingly advantageous as it relates to bacteria which are often carried by patients who have to be subjected to traumatic care, syringes, catheter or various operations. In this case, there is a very great danger sooner or later of infection immediately these patients enter into care.

It is therefore a pathogenic bacterium which is increasingly implicated in nocosomial infections in hospital environments, for example.

In fact, epidemiological surveillance of Staphylococcus aureus is becoming increasingly necessary and widespread.

The conventional medium for the detection of Staphylococcus aureus in the clinical field is a mannitol-salt medium which is based on the characteristics of resistance to salt and of acidification in the presence of mannitol. This test is not very satisfactory, in particular as regards sensitivity and specificity, this highly selective medium results in an excessively high number of false negatives and, furthermore, also gives false positives. Moreover, the staining of the colonies originating from the acidification spreads into the medium, which does not facilitate the reading when the sample is not a pure culture and when isolated colonies are close to one another.

The prior art has already suggested the use of alternative media, in particular using phosphatase as feature for the detection of Staphylococcus aureus (Stevens D. L. and Jones C: Use of trehalose-mannitol-phosphatase agar to differentiate Staphylococcus aureus and Staphylococcus saprophyticus. J. Clin. Microbiol., 20, 977–980, 1984) with, for example, a medium comprising the phenolphthalein phosphate indicator. However, this medium exhibits the failing of giving a staining which can spread, which presents a problem when the sample is not a pure culture and, as in the preceding case, when the isolated colonies are close to one another.

The present invention is based on the use of a chromogenic medium comprising two chromogenic agents, making it possible to obtain a sensitive medium giving a virtually no false negatives for S. aureus and making it possible in addition to differentiate S. aureus from the other species, such as Streptococcus.

When it is indicated that a medium "does not give" or "gives virtually no" false positives or false negatives, it should always be understood that this is with respect to the strains which have been tested, it is not possible to be totally affirmative as atypical or mutant strains can appear every day.

More particularly, the invention relates to a medium for the detection of Staphylococcus aureus comprising, as chromogenic agent, at least one compound chosen from:

5-bromo-6-chloro-3-indoxyl phosphate and 5-bromo-4-chloro-3-indoxyl glucoside, in a culture medium, and additionally comprising deferoxamine.

Preferably, both chromogenic compounds will be used. When 5-bromo-6-chloro-3-indoxyl phosphate is used without the 5-bromo-4-chloro-3-indoxyl glucoside derivative, then use will preferably be made of a combination with a chromogenic substrate of glucosidase, generally of indoxyl glucoside type.

When 5-bromo-4-chloro-3-indoxyl glucoside is used without 5-bromo-6-chloro-3-indoxyl phosphate, use will preferably be made of a combination with a chromogenic substrate of phosphatase, generally of indoxyl phosphate type.

S. aureus culture media are known and are described in particular in the manual "Oxoïd Unipath Limited", Wade Road, Basingstoke, Hampshire, RG24 0PW, England. It can be, for example, "Nutrient Agar Oxoïd CM3", a medium based essentially on extracts of yeast, peptone and agar.

The term "chromogenic agent" is understood to denote a compound which changes color in the presence of a specific strain, in particular under the effect of the enzymatic system of said strain.

The use of the medium according to the invention makes it possible to observe a mauve staining of 5-bromo-6-chloro-3-indoxyl phosphate in the presence of S. aureus, whereas 5-bromo-4-chloro-3-indoxyl glucoside stains blue a large number of Streptococcus strains without staining Staphylococcus aureus.

This is entirely unexpected as the literature indicates that S. aureus is β-glucosidase positive, like numerous Streptococcus strains, this can be confirmed by using, for example, para-nitrophenyl β-glucoside. In point of fact, the surprising observation has been made that 5-bromo-4-chloro-3-indoxyl glucoside stains blue Streptococcus strains without staining Staphylococcus aureus strains, this has been confirmed with respect to a large number of S. aureus strains found in hospitals.

Furthermore, the presence of deferoxamine in the culture medium according to the present invention makes it possible to inhibit the growth of Staphylococcus epidermis without inhibiting Staphylococcus aureus, which makes it possible to distinguish these two organisms. The concentration used will preferably be between 0.010 and 0.100 g/l.

The medium according to the present invention can also be improved by adding one or both of the following chromogens:

5-bromo-4-chloro-3-indoxyl galactoside and 5-bromo-4-chloro-3-indoxyl glucuronide, which are two features negative for Staphylococcus aureus and thus make it possible to differentiate it from the strains positive for these chromogens.

The media according to the present invention will comprise preferably from 0.01 to 0.500 g/l, in particular from 0.050 to 0.150 g/l, of 5-bromo-6-chloro-3-indoxyl phosphate, preferably from 0.010 to 0.200 g/l of 5-bromo-4-chloro-3-indoxyl glucoside, preferably from 0.010 to 0.200 g/l of 5-bromo-4-chloro-3-indoxyl galactoside and preferably from 0.010 to 0.200 g/l of 5-bromo-4-chloro-3-indoxyl glucuronide.

A preferred medium according to the invention, which makes it possible to differentiate Staphylococcus aureus microorganisms by the mauve staining of the colonies, whereas other strains are inhibited or give colorless or blue colonies, is as follows:

| | |
|---|---:|
| Peptone and yeast extract | 50 g/l |
| 5-bromo-6-chloro-3-indoxyl phosphate | 0.100 g/l |
| 5-bromo-4-chloro-3-indoxyl glucoside | 0.050 g/l |
| 5-bromo-4-chloro-3-indoxyl galactoside | 0.050 g/l |
| 5-bromo-4-chloro-3-indoxyl glucuronide | 0.050 g/l |
| Deferoxamine | 0.050 g/l |
| Agar | 15 g/l |

Other characteristics and advantages of the present invention will become apparent on reading the examples below:

EXAMPLES

In order to demonstrate the advantage of the use of 5-bromo-6-chloro-3-indoxyl phosphate in revealing S.

*aureus*, it is compared below with the same type of phosphate chromogen but this time 5-bromo-4-chloro-3-indoxyl phosphate.

The results are shown in the following table:

|  | Color of the colonies after 24 hours at 37° C. | |
| --- | --- | --- |
|  | Medium A | Medium B |
| S. *aureus* AR 3916 | blue | mauve |
| S. *aureus* AR 3917 | colorless | mauve |
| S. *aureus* AR 3918 | blue | mauve |

Medium A
- Nutrient Agar Oxoïd CM3 28 g/l,
- 5-bromo-4-chloro-3-indoxyl phosphate 0.050 g/l Medium B
- Nutrient Agar Oxoïd CM3 28 g/l,
- 5-bromo-6-chloro-3-indoxyl phosphate 0.050 g/l It is observed that, although the two chromogens are extremely similar, the substrate 5-bromo-6-chloro-3-indoxyl phosphate makes it possible, in comparison with the corresponding 5-bromo-4-chloro- derivative, to exclude false negatives with regard to the AR 3917 strain.

What is claimed is:

1. A medium for the detection of *Staphylococcus aureus*, characterized in that it comprises, in a *Staphylococcus aureus* culture medium, at least one of the following two chromogenic agents:

5-bromo-6-chloro-3-indoxyl phosphate and
   5-bromo-4-chloro-3-indoxyl glucoside, and in that it additionally comprises deferoxamine.

2. The medium as claimed in claim 1, characterized in that it comprises both chromogenic agents.

3. The medium as claimed in either of claims 1 and 2, characterized in that it additionally comprises at least one of the following two chromogenic agents:

5-bromo-4-chloro-3-indoxyl galactoside and
   5-bromo-4-chloro-3-indoxyl glucuronide.

4. The medium as claimed in one of claims 1 to 3, characterized in that it comprises:

| | |
| --- | --- |
| Peptone and yeast extract | 50 g/l |
| 5-bromo-6-chloro-3-indoxyl phosphate | 0.100 g/l |
| 5-bromo-4-chloro-3-indoxyl glucoside | 0.050 g/l |
| 5-bromo-4-chloro-3-indoxyl galactoside | 0.050 g/l |
| 5-bromo-4-chloro-3-indoxyl glucuronide | 0.050 g/l |
| Deferoxamine | 0.050 g/l |
| Agar | 15 g/l |

* * * * *

UNITED STATES PATENT AND TRADEMARK OFFICE
CERTIFICATE OF CORRECTION

PATENT NO. : 6,548,268 B1
DATED : April 15, 2003
INVENTOR(S) : Rambach

It is certified that error appears in the above-identified patent and that said Letters Patent is hereby corrected as shown below:

Title page,
Item [57], ABSTRACT, please delete "The invention concerns a novel chromogenic medium for isolating *Staphylococcus aureus*, characterised in that it comprises in a culture medium of *Staphylococcus aureus* at least one of the following two chromogenic agents: 5-bromo 6-chloro 3-indoxyl phosphate and 5-brono 4-chloro 3-indoxyl glucoside and it further contains deferoxamine." and insert -- The invention provides a chromogenic medium for isolating *Staphylococuus aureus*, characterized in that the medium comprises in a culture of *Staphylococcus aureus* at least one of the following two chromogenic agents: 5-bromo-6-chloro-3-indoxyl phosphate and 5-bromo-4-chloro-3-indoxyl glucoside and additionally comprises deferoxamine. --

Column 3,
Line 27, please delete "A medium" and insert -- A chromogenic medium --.
Line 28, please delete "that is comprises" and insert -- that said medium comprises --.

Column 4,
Line 5, please delete "it additionally" and insert -- said medium additionally --.
Lines 7, 9 and 14, please delete "it" and insert -- said medium --.

Signed and Sealed this

Twenty-eighth Day of December, 2004

JON W. DUDAS
*Director of the United States Patent and Trademark Office*